United States Patent [19]

Yamane et al.

[11] Patent Number: 6,149,894
[45] Date of Patent: Nov. 21, 2000

[54] METHOD FOR THE MANUFACTURE OF TOOTHPASTE

[75] Inventors: Odete T. Yamane; Fernanda C. G. Correa; Rosangela Takako Morisita, all of S. Paulo, Brazil

[73] Assignee: Colgate Palmolive Company, New York, N.Y.

[21] Appl. No.: 09/312,287

[22] Filed: May 14, 1999

[51] Int. Cl.$^7$ ....................................................... A61K 7/16
[52] U.S. Cl. .................................................................. 424/49
[58] Field of Search ........................................ 424/49–58

[56] References Cited

U.S. PATENT DOCUMENTS

| | | |
|---|---|---|
| 2,751,328 | 6/1956 | Sanders ...................................... 424/49 |
| 4,599,363 | 7/1986 | Miles et al. ................................ 424/49 |
| 4,795,630 | 1/1989 | Okouchi et al. ........................... 424/49 |
| 5,236,696 | 8/1993 | Catiis et al. ............................... 424/49 |
| 5,320,832 | 6/1994 | Catiis et al. ............................... 424/49 |

*Primary Examiner*—Shep K. Rose
*Attorney, Agent, or Firm*—Paul Shapiro

[57] ABSTRACT

A method is disclosed for the manufacture of a toothpaste containing an ingredient mixture of a calcium carbonate abrasive, a thickener and an aqueous humectant wherein there is sequentially added the calcium carbonate abrasive dispersed in a high solids aqueous dispersion containing 50 to 80% by weight calcium carbonate to the aqueous humectant and thereafter adding the binder and binding the ingredients before any further ingredients are added to the mixture to produce the toothpaste.

5 Claims, No Drawings

METHOD FOR THE MANUFACTURE OF TOOTHPASTE

BACKGROUND OF THE INVENTION

1. Field of the Invention

This invention relates to the manufacture of toothpastes and more particularly to a method of manufacturing a toothpaste which contains an abrasive system comprised at least in part of calcium carbonate.

2. The Prior Art

Dentifrices, such as toothpaste are generally extrudable pastes containing insoluble abrasives that aid in the removal of plaque, stains and other deposits from the teeth and help to polish them. Toothpaste compositions contain a variety of ingredients, the major types of ingredients generally being abrasive particulates,, a thickening agent, a liquid vehicle and surfactant. Other ingredients include flavoring agents and various other constituents for cosmetic, therapeutic or aesthetic effects.

Abrasives suitable for use in toothpaste compositions are generally finely divided, water-insoluble powdered materials such as silica, dicalcium phosphate dihydrate, calcium carbonate or calcined alumina. The toothpaste generally consists of a suspension of the abrasive in an aqueous humectant liquid phase. In order to hold the solid and liquid ingredients in the form of a stable paste with desirable rheological properties, the toothpaste invariably also includes a thickener or binder. A large number of different thickeners are known to the art and include, carboxymethylcellulose, xanthan gum, guar gum, carrageenan and mixtures thereof as thickener systems for toothpaste.

When preparing toothpastes, the toothpaste manufacturer encounters certain difficulties using abrasive powders and thickener systems to make a consumer acceptable toothpaste. For example, handling problems are encountered with the powdered abrasive where the particulate solids represent 10–60% by weight of the total toothpaste product and wherein the powders are low in bulk density which causes powder loss on debagging and during addition to the ingredient mixing tank. Also, upon the addition of the abrasive powder to the other ingredients in the mixing tank, there is a strong tendency towards lumping when combined with the water and humectant liquids present therein

SUMMARY OF THE INVENTION

In accordance with the present invention, a method is provided for the rapid, lump-free addition of calcium carbonate abrasive powders used for the preparation of toothpaste compositions wherein the powders constitute a major portion of the product, which method is a marked simplification of earlier powder addition techniques and comprises charging the water and humectant vehicle ingredients of the toothpaste to a mixing tank, introducing the abrasive calcium carbonate powder as a high solids slurry, in the order of 50–80% by weight solids, directly into the liquid vehicle and thereafter subjecting the ingredient mixture to homogenization by intimate mixing followed sequentially by the addition of a thickener and additional water to adjust the rheology of the paste product to the desired extrudible consistency.

It is critical to the practice of the present invention that the thickener ingredient be added to the water/humectant liquid vehicle after the addition of the abrasive slurry as the reverse sequence will cause a viscous gel to form which is difficult to subject to further processing. It is further critical to the method of the present invention that any further water addition to adjust the toothpaste rheology be made after the addition of the thickener so that a lump-free, smooth textured toothpaste product is obtained.

In a preferred embodiment of the invention, an essentially smooth, lump-free dentifrice paste is obtained in accordance with the above described method by first introducing a liquid vehicle comprised of a humectant such as glycerol, liquefied sorbitol (generally a 70% aqueous solution) or other liquid polyols, followed in sequence by the addition of the calcium carbonate abrasive slurry, a thickener such as carboxymethylcellulose and then water to a mixing tank and thereafter subjecting the ingredients to a continuous vacuum and intimate mixing between each sequence to prepare a homogeneous paste mixture.

The liquid vehicle of the dentifrice paste products made in accordance with the present invention is generally a humectant/water mixture, and will generally be present in the final paste product in the range of from about 10 to 85% by weight, with from 30–70% being a preferred range for toothpastes. Humectants used in dentifrice formulations are well known in the art and include glycerine, sorbitol, propylene glycol, polyethylene glycol, mannitol, polypropylene glycols, and mixtures thereof.

Stable aqueous calcium carbonate slurries used in the method of the present invention generally contain about 50 to about 80% by weight calcium carbonate. Such slurry materials are available commercially and are widely used in the paper making industry; calcium carbonate being a pigment which is excellent in whiteness and has affinity for ink, gloss and printability.

Inorganic dispersants which may be used to stabilize the calcium carbonate slurry include such condensed phosphates as pyrophosphates, tripolyphosphates, trimetaphosphates, tetrametaphosphates, and hexametaphosphates, zinc salts and silicates. Organic dispersants, include polycarboxylates such as polyacrylates, polymethacrylates, and polymaleates and polyvinyl alcohol. Such dispersants are known to the art, for example, U.S. Pat. No. 4,818,783 discloses dispersing calcium carbonate in an aqueous medium containing as the dispersant (1) 0.1 to 2 parts by weight of (a) a carboxyl group-containing water-soluble polymer possessing a number average molecular weight in the range of 2,000 to 80,000 and (b) a water soluble condensed phosphate and (2) 0.03 to 1 part by weight of a water soluble anionic modified polyvinyl alcohol respectively based on 100 parts by weight of the calcium carbonate.

The content of calcium carbonate abrasive in the final paste product will range from about 20 to about 75% and preferably about 30 to about 60% by weight.

Thickeners that can be used in accordance with the method of the present invention preferably include the natural and synthetic gums and gum-like materials, desirably carboxyl methyl cellulose sodium carboxymethylcellulose, hydroxyethylcarboxymethylcellulose, carrageenin, gum tragacanth, xanthan gum, guar gum, alginates, bentonite and other natural clays and synthetic inorganic clays. The gums are hydratable or gelled with water or alkanols, especially with polyhydric alcohols such as glycerol and sorbitol.

The proportions of thickeners present in the toothpaste product of the present invention will generally be in the range of from 0. 1-to about 5% by weight of the final product and in the case of synthetic gums such as sodium carboxymethylcellulose, the range will preferably be from about 0.1 to 3%.

Inorganic thickening agents suitable for use in the present invention include colloidal silicas having bodying properties, such as the aerogels Syloid 244 and 266 (available from W. R. Grace Company), Aerosil (available from DeGussa Co.) and pyrogenic silicas sold under the tradename Cab-O-Sils (available from Cabot Corporation). Tixosil 333 and Tixosil 43B (available from Rhodia Ltda.), Zeodent 165 (available from J. M. Huber Corporation).

In the manufacture of the toothpaste in accordance with the method of the present invention, mixing of the ingredients is accomplished in mixing vessels conventionally used and equipped for the manufacture of toothpaste. The ingredients may be charged to mixer at an elevated temperatures for example 45to 70° C., but is preferably performed at room temperature to save heating and cooling times.

Once the homogeneous paste containing the aqueous humectant, abrasive and thickener is prepared, which can generally be referred to as a base paste, various other classes of ingredients may be added to finalize the toothpaste product, which additional ingredients generally include surfactants, silica aerogels or other colloidal silicas, therapeutic agents, preservatives and flavoring agents or other ingredients that will finalize the desired toothpaste product.

Examples of surfactants useful in the toothpastes prepared in accordance with the method of the present invention include anionic surfactants such as sodium alkylsulfates (sodium laurylsulfate, sodium myristylsulfate), sodium N-acylsarcosinates (sodium N-lauroylsarcosinate, sodium N-myristoylsarcosinate, N-acylglutamic acid salts (sodium N-palmitoylglutamate, etc.), and sulfosuccinic acid surfactants (polyoxyethylene alkyl disodium sulfosuccinate, dialkyl sodium sulfosuccinate).

Examples of nonionic surfactants usable in the method of the present invention include sugar fatty acid esters (sucrose fatty acid ester, maltose fatty acid ester, lactose fatty acid ester, etc.), polyoxyethylene alkyl ethers, polyoxyethylene sorbitan fatty acid esters (polyoxyethylene sorbitan mono laurate, polyoxyethylene sorbitan monostearate, etc.), polyoxyethylene fatty acid esters (polyoxyethylene-hardened castor oil, etc.), sorbitan fatty acid esters, fatty acid monoglycerides and polyoxyethylene/polyoxypropylene block copolymers.

Examples of amphoteric surfactants usable herein include N-alkyldiaminoethylglycine (N-lauryldiaminoethylglycine, N-myristyldiethylglycine, etc.), N-alkyl-N-carboxymethylammonium betaine, 2-alkyl-1-hydroxyethylimidazoline betaine sodium and lauryldimethylaminoacetic acid betaine.

Either one of the above described surfactants or a mixture of two or more thereof may be used to prepare the toothpaste composition of the present invention at a concentration ranging from 0.1 to 10% by weight based on the whole composition.

The toothpaste compositions prepared in accordance with the process of the present invention may also contain flavors such as menthol, arvensis mint oil, synthetic mint flavors, carvone, eugenol, methyleugenol, methyl salicylate, methyl eugenol, thymol, anethole, limonene, ocimene, n-decyl alcohol, citronellol, .alpha.-terpineol, linalol, ethyllinalol, vanillin, thyme, nutmeg, spearmint oil, peppermint oil, lemon oil, orange oil, sage oil, rosemary oil, cinnamon oil, winter green oil, clove oil and eucalyptus oil. Either one of these flavors or a mixture of two or more thereof may be used. The content thereof ranges from 0.1 to 5% by weight, preferably from 0.5 to 2% by weight, based on the whole composition.

The toothpaste compositions of the present invention may also contain sweeteners such as saccharin sodium, acesulfame potassium, glycyrrhizin, perillartine, thaumatin, aspartylphenylalanyl methyl ester and xylitol. The content of the sweeteners ranges from 0.01 to 1% by weight, preferably from 0.05 to 0.5% by weight, based on the whole composition.

The toothpaste composition prepared in accordance with the method of the present invention may furthermore contain therapeutic ingredients such as water-insoluble noncationic antibacterial agents such as triclosan, Vitamin E analogs (dl-.alpha.-tocopherol acetate, tocopherol succinate, tocopherol nicotinate, etc.), Vitamin A (retinol, alpha carotene, beta carotene), Vitamin B (B1-thyamin, B2-riboflavine, B3-niacine, B5-pantothenic acid, B6-pirydoxine, B7-biotine, B8/B9/Bc-folic acid, B12-cianocobalamine), Vitamin C (ascorbic acid, sodium ascorbate), cationic antibacterial agents (chlorhexidine hydrochloride, cetylpyridinium chloride), enzymes (dextranase, amylase, protease, mutanase, lysozyme), herbal extracts/oils (chamomile, myrrh, eugenol, tea tree oil, sage oil, mallow, eucalyptus, melissa, pomegranade, apricot, millefolium extract, tangerine extract), natural ingredients (algae, propolis), anticavity alkali metal agents and monofluorophosphates (sodium monofluorophosphate, potassium monofluorophosphate, etc.), fluorides (sodium fluoride, stannous fluoride, etc.), whitening agents (aluminum oxide, calcium peroxide), debriding agent (sodium bicarbonate), astringent salts (such as zinc), chlorophyll, and preservatives such as methyl paraben, tooth desensitizing agents such as potassium and stronthium salts, condensed antitartar phosphates such as sodium and potassium tetrapyrophosphate, pigments (Blue 15-CI74160, Green 7-CI74260, Red 4-CI12085, Yellow 115 CI47005:1), dyes (Red 40 CI16035,Red 33 CI17200, Red 3 C145430, Carmine 5 CI75470, Blue 1 CI42090, Yellow 5 CI19140, Yellow 10 C147005) Mica and Speckles. Use can be made of either one of these ingredients or a mixture of two or more thereof in amounts ranging from 0.001 to abut 15% by weight of the toothpaste.

The following Example is illustrative of the invention. All percentages are by weight.

EXAMPLE

A toothpaste was made according to the following formula:

|  | % Weight |
| --- | --- |
| Sorbitol | 20.00 |
| Carboxymethylcellulose (CMC) | 1.20 |
| Irradiated water | 5.020 |
| Calcium carbonate (65% by weight slurry) | 63.080 |
| Sodium saccharin | 0.200 |
| Methylparaben | 0.100 |
| Ethyl alcohol | 1.500 |
| Sodium silicate | 1.000 |
| Sodium monofluorophosphate | 1.140 |
| Sodium lauryl sulfate (SLS) 29% solution | 5.600 |
| Flavor | 1.160 |

The toothpaste was made in Frima Mixer toothpaste mixer. Mixing was carried out under vacuum of 600–680 mm Hg. The mixing steps were as follows:

Stage 1—The sorbitol was put in the mixer.
Stage 2—Half the water content was added to the mixer.
Stage 3—The calcium carbonate slurry, containing 65% by weight calcium carbonate, available from Quimbarra Company, Rio de Janeiro, Brazil stabilized with sodium silicate and sodium hexametaphosphate dispersants was drawn into the mixer. Mixing took place for about 1 minute to prepare a homogeneous dispersion.

Stage 4—A suspension of CMC thickener and the preservative, methyl paraben in ethanol prepared in a separate mixing vessel, was added to the mixer and mixed for 15 minutes, with a mixing anchor speed of 22 rpm.

Stage 5—A solution of sodium saccharin and sodium monofluorophosphate was prepared with the remainder of the water in a separate vessel and added to the mixer and mixed for 2 minutes to produce a smooth cream.

Stage 6—Sodium silicate was added to the mixer.

Stage 7—The flavor was added to the mixer and mixed for 2 minutes.

Stage 8—SLS was added and mixed for 20 minutes.

The toothpaste prepared in accordance with the sequential steps described above had a satisfactory smooth texture and acceptable appearance. A comparative toothpaste, which was not made by the method of this invention, that is Stage 4, was performed before Stage 3 or Stage 5 was performed before Stage 4, resulted in a toothpaste product that had a rough granular texture. The coarse texture of the toothpaste ribbon, especially noticeable when spread with the finger, meant that the product was of poor quality. The toothpaste ribbon lacked the uniformly smooth texture required of an acceptable commercial product.

What is claimed is:

1. A method for making a toothpaste containing an ingredient mixture of a calcium carbonate abrasive, a thickener and an aqueous humectant which comprises sequentially adding to a mixing tank the calcium carbonate abrasive dispersed in a high solids aqueous dispersion containing about 50 to about 80% by weight calcium carbonate to the aqueous humectant and thereafter adding to the tank the thickener and mixing the ingredients calcium carbonate and humectant before any further ingredients are added to the mixture in the tank to produce the toothpaste, whereby a toothpaste of uniformly smooth texture is obtained.

2. The method of claim 1 wherein the thickener is carboxymethyl cellulose.

3. The method of claim 1 wherein the humectant is sorbitol.

4. The method of claim 1 wherein the content of calcium carbonate in the toothpaste ranges from about 20 to about 70% by weight.

5. The method of claim 1 wherein the thickener is present in the toothpaste at a concentration of about 0.1 to about 5% by weight.

* * * * *